(12) United States Patent
Fidge et al.

(10) Patent No.: US 10,918,107 B2
(45) Date of Patent: Feb. 16, 2021

(54) ENCAPSULATED LACTAMS

(71) Applicant: Conopco, Inc., Englewood Cliffs, NJ (US)

(72) Inventors: Christopher Fidge, Wirral (GB); Stephen Golding, Northwich (GB); Paul Damien Price, Wirral (GB); David William Thornthwaite, Little Neston (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/730,964

(22) Filed: Dec. 30, 2019

(65) Prior Publication Data

US 2020/0128826 A1 Apr. 30, 2020

Related U.S. Application Data

(63) Continuation of application No. 15/750,893, filed as application No. PCT/EP2016/067613 on Jul. 25, 2016, now abandoned.

(30) Foreign Application Priority Data

May 20, 2015 (GB) .................................. 15181842

(51) Int. Cl.
*A01N 43/36* (2006.01)
*A01N 25/04* (2006.01)
(Continued)

(52) U.S. Cl.
CPC ............. *A01N 43/36* (2013.01); *A01N 25/02* (2013.01); *A01N 25/04* (2013.01); *A01N 25/26* (2013.01);
(Continued)

(58) Field of Classification Search
CPC ...... A01N 43/36; A01N 25/04; A61K 8/4913; A61K 8/87; A61K 8/11; A61Q 5/02; A61Q 11/00
See application file for complete search history.

(56) References Cited

U.S. PATENT DOCUMENTS

| 5,955,419 A | 9/1999 | Barket, Jr. et al. |
| 7,985,722 B2 | 7/2011 | DeSanto |

(Continued)

FOREIGN PATENT DOCUMENTS

| CN | 1169112 | 12/1997 |
| CN | 1688543 | 10/2005 |

(Continued)

OTHER PUBLICATIONS

Wei et al.; Measurement and Correlation of the Solubility of Penicillin V Potassium in Ethanol + Water and 1-Butyl Alcohol + Water Systems; Journal of Chemical and Engineering Data; 2015; 112-117; vol. 60, No. 1.

(Continued)

*Primary Examiner* — Jianfeng Song
(74) *Attorney, Agent, or Firm* — Foley & Lardner LLP

(57) ABSTRACT

A method of measuring a wet friction of a bundle of hair, using a system which includes a friction probe having a contact surface and fitted with a weight in the range of from 10 g to 500 g, inclusive, a means for securing the bundle of hair, and a water bath, the friction probe being connected to a texture analyser, the method including the step of i) providing a bundle of hair fibres. The method also includes the steps of ii) aligning the bundle of hair fibres; iii) securing the bundle of hair fibres; iv) immersing the bundle of hair fibres under water in the water bath; v) contacting the bundle of hair fibres with the contact surface of the friction probe, which is fitted with the weight; vi) moving the probe along (Continued)

A = Carrier/Lactam/NCO
B = Surfactant/Stabiliser the hair fibres; and vii) recording the friction generated under step vi).

11 Claims, 1 Drawing Sheet

(51) Int. Cl.

| | |
|---|---|
| *A01N 25/02* | (2006.01) |
| *A61Q 17/00* | (2006.01) |
| *A01N 25/26* | (2006.01) |
| *A61K 8/11* | (2006.01) |
| *A61K 8/87* | (2006.01) |
| *A61K 8/49* | (2006.01) |
| *A61Q 11/00* | (2006.01) |
| *A61Q 5/02* | (2006.01) |

(52) U.S. Cl.
CPC .............. *A61K 8/11* (2013.01); *A61K 8/4913* (2013.01); *A61K 8/87* (2013.01); *A61Q 17/005* (2013.01); *A61Q 5/02* (2013.01); *A61Q 11/00* (2013.01)

(56) References Cited

U.S. PATENT DOCUMENTS

| | | | |
|---|---|---|---|
| 8,641,948 B2 | 2/2014 | Ghogh et al. | |
| 9,586,901 B2 | 3/2017 | Kumar et al. | |
| 9,930,888 B2 | 4/2018 | Parry et al. | |
| 10,306,886 B2 | 6/2019 | Price | |
| 2007/0269473 A1* | 11/2007 | Nelson ................ | A23L 27/13 424/408 |
| 2009/0175810 A1 | 7/2009 | Winckle | |
| 2011/0059144 A1* | 3/2011 | Fletcher ............... | A61K 8/11 424/401 |
| 2012/0190667 A1 | 7/2012 | Ghogh et al. | |
| 2013/0142855 A1 | 6/2013 | Gross et al. | |
| 2013/0190377 A1 | 7/2013 | Kumar et al. | |
| 2013/0330292 A1 | 12/2013 | Lei et al. | |
| 2014/0017287 A1* | 1/2014 | Lei ...................... | A61K 8/84 424/401 |
| 2014/0294925 A1 | 10/2014 | Yin | |
| 2014/0296336 A1 | 10/2014 | Berndl et al. | |
| 2015/0073069 A1 | 3/2015 | De Gans et al. | |
| 2015/0351393 A1 | 12/2015 | Parry et al. | |

FOREIGN PATENT DOCUMENTS

| | | |
|---|---|---|
| CN | 1688543 A | 10/2005 |
| CN | 101410372 | 4/2009 |
| CN | 101932300 | 12/2010 |
| CN | 102257117 | 11/2011 |
| CN | 102257117 A | 11/2011 |
| CN | 103260609 | 8/2013 |
| CN | 102257117 B | 12/2014 |
| EP | 0000010 A1 | 12/1978 |
| EP | 0000011 A1 | 12/1978 |
| EP | 0000014 A1 | 12/1978 |
| EP | 0000017 A1 | 12/1978 |
| EP | 0000023 A1 | 12/1978 |
| EP | 0000010 B1 | 1/1980 |
| EP | 0000011 B1 | 4/1980 |
| EP | 0000023 B1 | 7/1980 |
| EP | 0000017 B1 | 9/1981 |
| EP | 0000011 B2 | 8/1983 |
| WO | 2004016588 A1 | 2/2004 |
| WO | WO2004016588 | 2/2004 |
| WO | 2006085089 A1 | 8/2006 |
| WO | WO2006085089 | 8/2006 |
| WO | WO2007008504 | 1/2007 |
| WO | 2007085042 A1 | 8/2007 |
| WO | WO2007085042 | 8/2007 |
| WO | 2010069742 A1 | 6/2010 |
| WO | WO2010069742 | 6/2010 |
| WO | WO2012156250 | 11/2012 |
| WO | 2014118240 A1 | 8/2014 |
| WO | WO2014118240 | 8/2014 |
| WO | WO2017029112 | 2/2017 |

OTHER PUBLICATIONS

Guedes et al.; Solid Dispersions of Imidazolidinedione by PEG and PVP Polymers with Potential Antischistosomal Activities; PharmSciTech; Mar. 1, 2011; pp. 401-410; vol. 12, No. 1.
Chadha et al.; Analytical techniques used to characterize drug-polyvinylpyrrolidone systems in solid and liquid states—An overview; J Scientific and Industrial Research; Jun. 1, 2006; pp. 459-469; vol. 65.
Kim et al.; Solid Dispersions as a Drug Delivery System; J Pharmaceutical Investigation; Mar. 29, 2011; pp. 125-142; vol. 41, No. 3.
Search Report in EP15181842; dated Dec. 10, 2015.
Written Opinion in EP15181842; dated Dec. 10, 2015.
Written Opinion in EP15181851; dated Dec. 11, 2015.
Mary E. Davey et al.; Rhamnolipid Surfactant production Affects Biofilm Architecture in Pseudomonas aeruginosa PAO1; Journal of Bacteriology; Feb. 1, 2003; pp. 1027-1036; vol. 185, No. 3; American Society for Microbiology.
Written Opinion in EP15181846; dated Dec. 11, 2015.
Ondrej Krenk et al.; Methodology for Synthesis of Enantiopure 3,5-Disubstituted Pyrrol-2-ones; European Journal of Organic Chemistry; 2015; pp. 5414-5423; XP002752111.
Search Report in EP15181858; dated Dec. 11, 2015.
Written Opinion in EP15181858; dated Dec. 11, 2015.
Search Report in EP15181856; dated Dec. 14, 2015.
Written Opinin in EP15181856; dated Dec. 14, 2015.
Written Opinion in EP15181847; dated Dec. 17, 2015.
Search Report in EP15181851; dated Dec. 11, 2015.
Search Report in EP15181847; dated Dec. 17, 2015.
Carla S.M. Pereira et al.; Ethyl lactate as a solvent: properties, applications and production processes—a review; Green Chemistry; 2011; pp. 2658-2671; XP055235519; vol. 13, No. 10.
Search Report in EP15181846; dated Dec. 11, 2015.
Search Report & Written Opinion in EP15181849; dated Feb. 23, 2016.
Von R. Scheffold Und P. Dubs; Synthese von Azaprotoanemoninen; Helvetica Chimica Acta; 1967; pp. 798-808.
Search Report and Written Opinion in PCTEP2016068625; dated Sep. 9, 2016.
Search Report & Written Opinion in PCTEP2016069072; dated Sep. 14, 2016.
Search Report and Written Opinion in PCTEP2016067616; dated Sep. 12, 2016.
Search Report and Written Opinion in PCTEP2016067613; dated Sep. 21, 2016.
Search Report and Written Opinion in PCTEP2016068008; dated Sep. 12, 2016.
Search Report and Written Opinion in PCTEP2016068287; dated Oct. 26, 2016.
Search Report and Written Opinion in PCTEP2016068010; dated Sep. 12, 2016.
Search Report and Written Opinion in PCTEP2016068585; dated Oct. 4, 2016.
IPRP in PCTEP2016069072; Aug. 2, 2017.
Written Opinion 2 in PCTEP2016067613; dated Jul. 11, 2017.
IPRP2 in PCTEP2016068625; Sep. 6, 2017.
IPRP2 in PCTEP2016068585; Nov. 2, 2017.
Kerwin et al.; Polysorbate 20 and 80 Used in the Formulation of Protein Biotherapeutics: Structure and Degradation Pathways; Journal of Pharmaceutical Sciences; Aug. 2008; pp. 2924-2937; vol. 97; Wiley InterScience.
PTO-892 (Rev. Jan. 2001) Notice of References Cited Part of Paper No. 20190612.
PAO1, Journal of Bacteriology, 2003, pp. 1027-1036, vol. 185, No. 3, American Society for Microbiology.

(56) References Cited

OTHER PUBLICATIONS

Green Chemistry, 2011, pp. 2658-2671; XP055235519, vol. 13, No. 10.
Journal of Organic Chemistry, 2015, pp. 5414-5423; XP002752111.
1 and 1-Butyl Alcohol+ Water Systems; Journal of Chemical and Engineering Data; 2015; 112-117; vol. 60.
16 Search Report in EP15181842, dated Dec. 10, 2015.
17 Search Report in EP15181846, dated Dec. 11, 2015.
18 Search Report in EP15181847, dated Dec. 17, 2015.
19 Search Report in EP15181851, dated Dec. 11, 2015.
21 Search Report in EP15181858, dated Dec. 11, 2015.
25 Written Opinion in EP15181842, dated Dec. 10, 2015.
26 Written Opinion in EP15181846, dated Dec. 11, 2015.
27 Written Opinion in EP15181847, dated Dec. 17, 2015.
28 Written Opinion in EP15181851, dated Dec. 11, 2015.
29 Written Opinion in EP15181858, dated Dec. 11, 2015.
11 Search Report and Written Opinion in PCTEP2016068008, dated Sep. 12, 2016.
12 Search Report and Written Opinion in PCTEP2016068010, dated Sep. 12, 2016.
13 Search Report and Written Opinion in PCTEP2016068287, dated Oct. 26, 2016.
14 Search Report and Written Opinion in PCTEP2016068585, dated Oct. 4, 2016.
7 Search Report & Written Opinion in EP15181849, dated Feb. 23, 2016.
8 Search Report & Written Opinion in PCTEP2016069072, dated Sep. 14, 2016.
9 Search Report and Written Opinion in PCTEP2016067613, dated Sep. 21, 2016.
24 Written Opinion 2 in PCTEP2016067613, dated Jul. 11, 2017.
Borate et al.; Novel hybrids of fluconazole and furanones: Design, synthesis and antifungal activity; Bioorganic & Medicinal Chemistry Letters; 2011; pp. 4873-4878; vol. 21.
Munoz, et al.; Enzymatic enantiomeric resolution of phenylethylamines; Org. Biomol. Chem.; 2011; pp. 8171-8177 (abstract only—total 5 pages); vol. 9.
Luo Mingsheng, Gao Tianhu; Overview of Pharmaceutical Excipients; Overview of Pharmaceutical Excipients; 2006; pp. 627-628 (translation of relevant portions only).
Subbarao et al; Functions of Hydrotropes in Solutions; Chemical Engineering Technology; 2012; 225-237; 35(2).
Lin Hui, et al.; Micellization properties of different rhamnolipidic fractions and their solubilization; ACTA Scientiae Circumstantiae; 2011; 2609-2615 (with Engl. Abstract and human translation of pp. 2610 & 2614 only); 31, No. 12.
Kloeppel; Temperature inside collapsing bubble four times that of sun; News Bureau—Research, ; 2005; pp. 1-3.

\* cited by examiner

A = Carrier/Lactam/NCO
B = Surfactant/Stabiliser

ENCAPSULATED LACTAMS

CROSS-REFERENCE TO RELATED APPLICATIONS

This application claims priority to U.S. patent application Ser. No. 15/750,893, filed on Feb. 7, 2018, and International Patent Application No. PCT/EP2016/067613, filed on Jul. 25, 2016 and European Patent Application No. 15181842.4, filed on Aug. 20, 2015, all of which are incorporated herein by reference in their entireties.

This application claims priority from EP 15181842.4 filed 20 Aug. 2015 which is incorporated by reference for all purposes.

The present invention relates to encapsulated lactams. The encapsulated lactams are suitable for use in compositions, for example, in antimicrobial, anti-biofilm and bacteriostatic compositions. The invention further relates to methods of encapsulating lactams.

WO 2007/085042 and WO 2004/016588 disclose lactams for antimicrobial benefit and steps towards their synthesis. WO2014/118240 discloses antimicrobial compositions comprising a lactam and a hydrotope. US2011/0059144 relates to methods of improving the aesthetics of personal care compositions by encapsulating hydrophobic actives in a polyurea shell.

However, use of these lactams is limited by compatibility with certain formulations.

The present invention relates to encapsulated lactams. The encapsulation of the lactams permits greater flexibility of formulation as the encapsulation may permit use of the lactams in higher pH formulations and/or improve their solubility. In some cases, the encapsulation facilitates control and triggered release of lactams.

More specifically, the present invention relates to encapsulated lactams as described in WO 2007/085042 and WO 2004/016588, the contents of which, and in particular the lactam structures explicitly drawn out therein, are incorporated by reference.

For example, in a first aspect, the present invention relates to an encapsulated lactam of formula (I) or (II):

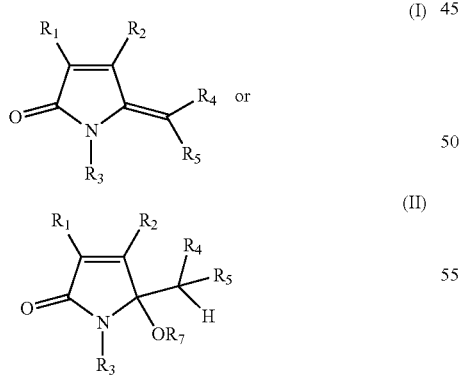

wherein:

$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and $R_3$ is selected from hydrogen, hydroxyl, alkyl, cycloalkyl, alkoxy, oxoalkyl, alkenyl, heterocyclyl, heteroaryl, cycloalkyl, aryl, aralalkyl and —C(O)CR$_6$=CH2;

$R_4$ and $R_5$ are independently selected from hydrogen, aryl, heterocyclyl, heteroaryl, and arylalkyl; and $R_6$ is selected from hydrogen and methyl; and $R_7$ is selected from hydrogen and —C(O)CR$_6$=CH$_2$; and Preferably, at least one of $R_4$ and $R_5$ is hydrogen.

It will be appreciated that, where appropriate groups may be optionally substituted. Optional substituents may include halogens, $C_{1-4}$alkyl, $C_{1-4}$haloalkyl (for example, $CF_3$) and $C_{1-4}$alkoxy.

Alkyls may, for example, be $C_{1-12}$alkyls, such as $C_{1-6}$alkyls. Aryls may, for example, be $C_{6-10}$aryls, for example, phenyls.

Preferably, at least one of $R_1$ and $R_2$ is selected from heterocyclyl, heteroaryl, aryl and arylalkyl.

Preferably, $R_1$ is hydrogen. Preferably, $R_3$ is hydrogen. Preferably, $R_4$ is hydrogen. Preferably, $R_5$ is hydrogen. Preferably, $R_6$ is hydrogen. Preferably, $R_7$ is hydrogen. Preferably, $R_2$ is aryl or aralalkyl. More preferably, $R_2$ is a phenyl group or a substituted phenyl group, for example, a mono-substituted phenyl group. Substitution may be ortho, meta, or para. Preferably, it is para. Preferred substituents include halogen and methyl. For example, and without limitation, $R_2$ may be selected from phenyl, 4-fluorophenyl, 4-chlorophenyl, 4-bromophenyl and 4-methylphenyl.

Accordingly, in a first aspect, the present invention may provide an encapsulated lactam wherein the lactam is a lactam of Formula Ia or Formula IIa:

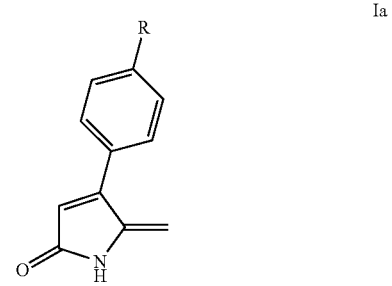

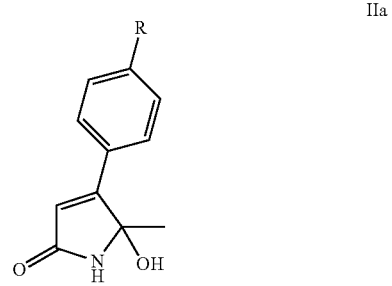

wherein R is H, halogen (preferably, F, Cl, or Br), or $C_{1-4}$alkyl (preferably methyl).

In some embodiments, the encapsulated lactam is a lactam of formula Ia. In some embodiments, the encapsulated lactam is a lactam of formula IIa.

Importantly, lactams of formula Ia have been found to be unstable in high pH7 conditions (high pH refers to a pH of at least 7). Encapsulation improves stability in these conditions, permitting the lactams to be used in a wider variety of compositions.

Preferred lactams may include:

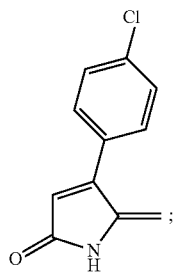

4-(4-chlorophenyl)-5-methylene-pyrrol-2-one (Ref. 488);

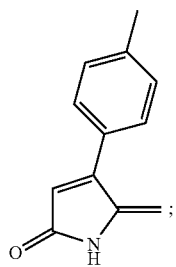

5-methylene-4-(p-tolyl)pyrrol-2-one (Ref. 491)

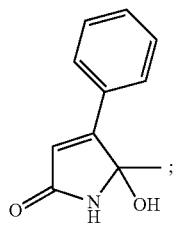

4-phenyl-5-hydroxy-5-methyl-1H-pyrrol-2-one (Ref. 131)

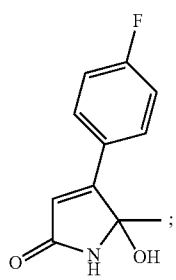

4-(4-fluorophenyl)-5-hydroxy-5-methyl-1H-pyrrol-2-one (Ref. 258)

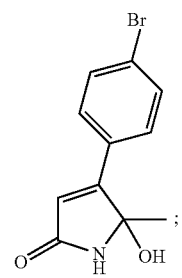

4-(4-bromophenyl)-5-hydroxy-5-methyl-1H-pyrrol-2-one (Ref. 316).

Suitably, the encapsulated lactam is a polymer encapsulated lactam.

The encapsulated lactam may be encapsulated in a polymer selected from a poly urea polymer, a melamine-formaldehyde copolymer; a urea formaldehyde copolymer and mixtures thereof.

The inventors have surprising found that lactams as described herein inhibit free radical polymerisation.

Accordingly, suitably the polymer is a condensation polymer.

For example, the polymer may be a condensation polymer of produced from a diamine and a disocyanate.

For example, the polymer may be or may comprise a polyurea of Formula P1:

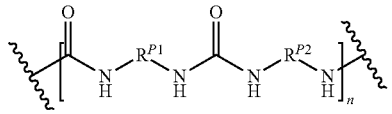

wherein $R^{P1}$ comprises a phenylene and $R^{P2}$ is an alkylene.

For example, $R^{P1}$ may be —$CH_2$-phenylene; in other words, the polymer may be derived from polymethylene polyphenyl isocyanate.

For example, $R^{P2}$ may be a straight chain alkylene of formula —$(CH_2)_m$—. In some cases, m is an integer from 2 to 10, for example from 2 to 8, for example from 4 to 8, for example, 6 (in other words, $R^{P2}$ may be hexylene).

In other words, the lactam may be encapsulated in a polymer formed from polymethylene polyphenyl isocyanate and hexamethylenediamine.

In some cases, the polymer and/or encapsulate structure is selected and/or configured to permit controlled or triggered release. For example, the encapsulate may dissolve at a pre-determined rate under certain conditions. For example, the encapsulate may release in response to a trigger. The trigger may be, for example, the presence or a certain concentration of acid, base, a salt, an enzyme; or a non-chemical trigger such as ultrasound or light.

Suitably, the lactam is encapsulated to form particles whose average diameter is from about 10 nanometers to about 1000 microns, preferably from about 50 nanometers to about 100 microns, more preferably from about 2 to about 40 microns, even more preferably from about 4 to 15 microns. A particularly preferred range is from about 5 to 10 microns, for example 6 to 7 microns. The capsule distribution can be narrow, broad or multimodal. Multimodal distributions may be composed of different types of capsule chemistries.

The encapsulation process suitably is done in a carrier oil, which may be a ketone. For example, the carrier oil may be a $C_{5-20}$alkyl ketone, for example a $C_{5-15}$alkyl ketone, for example a $C_{5-10}$alkyl ketone, for example a $C_{6-8}$alkyl ketone, such as a $C_7$alkyl ketone. The alkylketone may be branched or straight-chain. Preferably, it is straight chain. The oxo group of the alkyl ketone may be located at C2; in other words, the alkylketone may be an alkyl-2-one. A preferred carrier oil is 2-heptanone.

The obtained encapsulated lactam in carrier oil may be used as an additive for compositions.

Accordingly, in a second aspect the present invention relates to an additive comprising an encapsulated lactam. Suitably, the encapsulated lactam is in provided in a carrier oil. The lactam may be a lactam of Formula I or Formula II.

Accordingly, in a second aspect the present invention may provide an additive comprising an encapsulated lactam wherein the lactam is a lactam of Formula Ia or Formula IIa (wherein R is as defined herein) in a carrier oil.

Preferred lactams may be as described for the first aspect.

In some embodiments, the carrier oil is an alkylketone as described above. Preferably it is a $C_{5-10}$alkyl-2-one, most preferably it is heptan-2-one.

The encapsulated lactams are suitable for use in compositions. The composition may be, without limitation, any of a personal care composition, a homecare composition, a pharmaceutical composition, or an industrial composition such as an anti-biofilm coating or paint, for example, for use in maritime environments. The composition may also be an agricultural chemical. The compositions may be suitable for use as antimicrobial, anti-biofilm and bacteriostatic compositions. Non-limiting examples of such compositions are provided herein. The compositions may also be used as additive compositions; in other words, the composition may be combined with further ingredients such as excipients to form a composition as described above.

Accordingly, in a third aspect the present invention relates to compositions comprising an encapsulated lactam. The lactam may be a lactam of Formula I or Formula II.

Accordingly, in a third aspect the present invention may provide a composition comprising an encapsulated lactam of Formula Ia or IIa (wherein R is as defined herein).

Preferred lactams may be as described for the first aspect.

Advantageously, the composition may be a composition of pH ≥7, for example ≥8, for example ≥9, for example ≥10, for example ≥11.

Preferably the composition contains 0.000001 to 50% wt. lactam, more preferably 0.001 to 50% wt. even more preferably 0.01 to 5% wt, most preferably 0.01-2%.

In a fourth aspect, the present invention relates to method of encapsulating lactams, the method comprising interfacial polycondensation. The lactam may be a lactam of Formula I or Formula II, and the options and preferences described below may apply.

Accordingly, in a fourth aspect the present invention may provide a method of encapsulating a lactam of Formula Ia or IIb (wherein R is as described herein), the method comprising:
(a) combining said lactam with a carrier oil; then
(b) combining said lactam in carrier oil with a first polymerization agent; then
(c) combining the product of step (b) with an aqueous solution of a stabilizer;
(d) adding an aqueous solution comprising a second polymerization agent to the product of step (c) while stirring the mixture;

wherein the first and second polymerization agents form a polymer when they react with each other.

It will be appreciated that the carrier oil and aqueous solution are immiscible. The polymerization is therefore interfacial polycondensation.

The first polymerization agent may be an isocyanate. For example, it may be polymethylene polyphenyl isocyanate. The second polymerization agent may be a diamine, for example an α,ω-diamino $C_{2-10}$alkylene such as hexamethylenediamine.

Suitably, the lactam is dissolved in the carrier oil. Preferred carrier oils are described above. In other words, the product of step (a) is a solution. Suitably, the concentration of the solution is about 0.5 wt %. It may be higher. For example, it may be about 1 wt %. In some cases, the concentration of the solution is less than 5 wt %, suitably less than 3 wt %.

Suitably, step (c) includes vigorous agitation, for example homogenization. The speed may be greater than 5 k rpm, for example, greater than 10 k rpm. It may be around 15 k rpm. Suitably, the product of step (c) is an emulsion (i.e. the mixture may be emulsified).

Suitably, step (d) includes stirring, for example at up to 1000 rpm, up to 500 rpm. It may be 200-300 rpm. Step (d) may last around 1 hour.

The process may include a curing step (step (e)). For example, step (e) may comprise agitation of the product of step (d) for 1 hour, 2 hours, 3 hours, 4 hours, 5 hours. The agitation may use a bottle roller.

The stabilizer may be sulfonate, for example a naphthalene sulfonate such as an alkyl naphthalene sulfonate condensate (NSC). A commercially available example is Morwet-D425®, available from AkzoNobel® (Surface Chemistry).

It will be appreciated that options and preferences described with respect to the first aspect apply equally where possible to the other aspects, and vice versa.

FIGURES

DESCRIPTION

Figure 1:
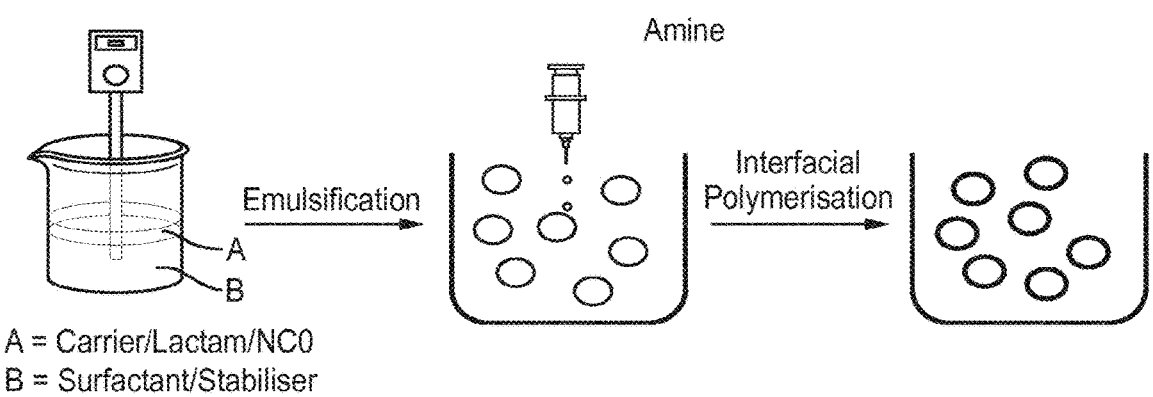
FIG. 1 shows a simple representation of encapsulation using an interfacial polycondensation method.

Lactams may be obtained using methods as described in WO 2007/085042 and WO 2004/016588, which are herein incorporated by reference in their entirety.

Compositions

The compositions described herein may be compositions having anti-microbial activity. In some cases, the compositions are anti-bacterial. They may have bactericidal and/or bacteriostatic activity. The inventor(s) have observed desirable bacteriostatic activity. Accordingly, in some cases, the composition is a bacteriostatic composition.

The compositions may also prevent and/or inhibit biofilm formation. Biofilms are formed when microorganisms stick to a surface. Biofilm extracellular polymeric substances may be formed. Biofilms (also referred to as slime) present problems in industrial environments; for example, they may form in pipes in apparatus, or industrial and agricultural structures, on solar panels, and on boat hulls and other marine structures. Biofilms may also pose a problem in domestic environments. For example, biofilms may form in domestic appliances such as washing machines. Biofilms are also present in personal care, for example, they may form on tooth surfaces.

Compositions suitable for any and all of these applications are within the scope of the invention. In some cases, the composition is a paint or other coating. In such cases, the composition may further comprise a binder, optionally a pigment and optionally one or more conventional additives (for example, to modify surface tension, improve flow properties, improve the finished appearance, increase wet edge, improve pigment stability, etc—such additives are known in the art). The composition may comprise an aqueous solvent or an organic solvent to suit purpose.

The composition may also be used in medical applications, for example to coat equipment including medical devices.

In some cases, the composition is a pharmaceutical composition. In other words, the composition may comprise a lactam as described herein and a pharmaceutically acceptable excipient. The composition may be suitable for topical use (for example, it may be a cream or lotion), it may be suitable for ocular use (for example, it may be an used as a pharmaceutical eye drop), it may be suitable for otic use (for example, it may be used as an ear drop), it may be suitable as a mouth wash, or it may be suitable for oral administration.

In some cases, the composition is a composition suitable for use in the home (often referred to as a homecare composition) or institutions. Homecare compositions include, without limitation, cleaning products, laundry detergents, and fabric conditioners. In some cases, the composition is a homecare composition, for example a laundry liquid. The composition may therefore comprise a detergent surfactant and a builder. The composition may be a fabric conditioner (also called a fabric softener) and may comprise an antistatic agent. The composition may also be a domestic cleaning product.

In some cases, the composition is a personal care composition. For example, the composition may be intended for use on the skin (for example, a cream, cleanser or serum). For example, the composition may be useful in the prevention or treatment of acne. For example, the composition may comprise one or more of dimethicone, petrolatum, a humectant such as hyaluronic acid or glycerin; and ceramide(s). The composition may be a deodorant/anti-perspirant composition. In some cases, the composition is a personal care composition comprising a detergent, for example, the composition may be a face wash or shower gel or hair shampoo. The composition may be a hair treatment composition other than a shampoo. The composition may be a deodorant composition (for example, a deodorant powder, paste or liquid). The composition may be an oral care composition (such as a toothpaste or mouthwash and may include, for example, fluoride and/or flavourings.

In some cases, the composition is a contact lens cleaning fluid.

The composition may be a composition suitable for use in agriculture, for example, as a soil additive (solid or liquid).

The composition may be a composition suitable for use in the treatment of or manufacture of glass or lens for example as an additive/treatment for solar panels.

Examples

The following syntheses are provided by way of illustration and exemplification, and not by way of limitation.

Encapsulation was achieved via an interfacial polycondensation method which can be represented simply as shown in FIG. 1.

The following representative example uses 4-(4-chlorophenyl)-5-methylene-pyrrol-2-one.

2-heptanone was used as the carrier (oil phase) for the lactam at a ratio of 1:199 (Lactam:Heptanone) which equates to 0.5% lactam solution. The inventor(s) have determined that the lactam is also soluble at 1%. The isocyanate was polymethylene polyphenyl isocyanate (Mn340) and the crosslinker was hexamethylenediamine (HMDA). Emulsification was carried out at a shear of 15K. The stabiliser is a commercial naphthalene sulphonate called Morwet-D425®. Morwet forms dark brown solutions so the encapsulated slurry is often buff/brown coloured.

PU Encapsulation Procedure

Preparation of Oil Phase A: 5 g (2-Heptanone:Lactam; 1:199) and 0.42 g isocyanate (PMDI, 340) were mixed in a 28 ml vial and agitated until fully dissolved.

Preparation of aqueous Phase B: 16 ml water containing 3 wt % MorwetD425 was prepared in a beaker.

Preparation of amine soln C: An aqueous HMDA solution (40%) was prepared.

Figure 2:
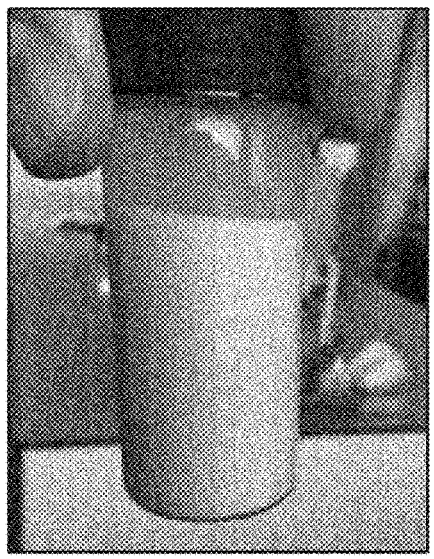
FIG. 2 shows a cured emulsion comprising an encapsulated lactam according to the invention.

Phase B was added to phase A under homogenization at 15 k rpm and then the mixture emulsified for 2 min (buff coloured emulsion obtained). Afterward, 1 ml of solution C was added dropwise into the emulsion over 1 min whilst stirring at 200-300 rpm. After 1 hour the sample slurry was placed on a bottle roller for approx. 5 hours to obtain a cured emulsion shown in FIG. 2.

Figure 3:
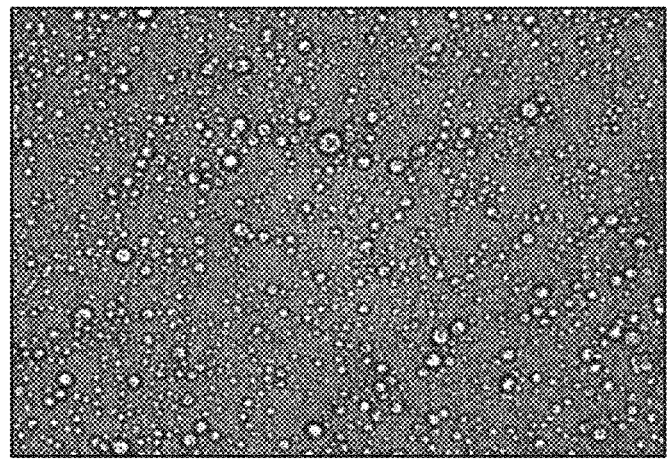
FIG. 3 shows a microscope picture of encapsulated particles according to the invention.

As can be seen from FIG. 3, encapsulated particles were obtained.

It will be appreciated that, except where expressly provided otherwise, all preferences are combinable.

We claim:

1. A polymer encapsulated lactam comprising a lactam of Formula Ia or Formula IIa:

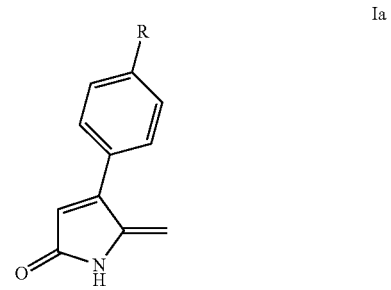

Ia

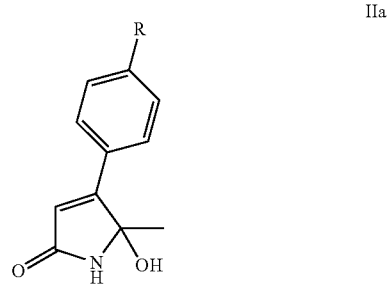

IIa wherein R is H, halogen, or C1-4alkyl, and the lactam is dissolved in a carrier oil comprising heptan-2-one; and the polymer is selected from a poly urea polymer, a melamine-formaldehyde copolymer, a urea formaldehyde copolymer and mixtures thereof.

2. The polymer encapsulated lactam of claim 1, wherein R is H, F, Cl, Br, or Me.

3. The polymer encapsulated lactam of claim 1, wherein the lactam is selected from:

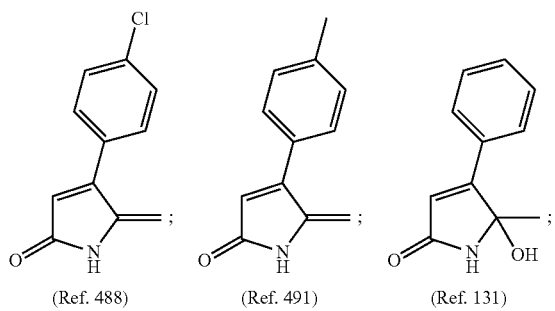

(Ref. 488)   (Ref. 491)   (Ref. 131)

-continued

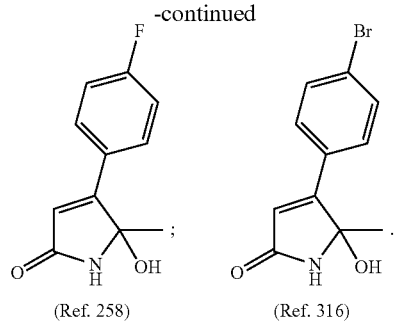

(Ref. 258)   (Ref. 316)

4. The polymer encapsulated lactam of claim 1 wherein the lactam is encapsulated in a polymer formed from polymethylene polyphenyl isocyanate and hexamethylenediamine.

5. The polymer encapsulated lactam of claim 1 having an average particle diameter of from 4 μm to 40 μm.

6. The polymer encapsulated lactam of claim 5 wherein the particles have a multimodal size distribution.

7. A composition comprising a polymer encapsulated lactam according to claim 1.

8. The composition of claim 7, wherein the composition contains 0.01 to 5% wt. lactam.

9. The composition of claim 7, wherein the composition contains 0.01 to 2% wt. lactam.

10. The composition of claim 7 wherein the composition further comprises water and has a pH greater than 7.

11. The composition of claim 10 further comprising a detergent.

* * * * *